United States Patent [19]
Holmes-Farley et al.

[11] Patent Number: 5,929,184
[45] Date of Patent: *Jul. 27, 1999

[54] HYDROPHILIC NONAMINE-CONTAINING AND AMINE-CONTAINING COPOLYMERS AND THEIR USE AS BILE ACID SEQUESTRANTS

[75] Inventors: Stephen Randall Holmes-Farley, Arlington; John S. Petersen, Acton, both of Mass.

[73] Assignee: GelTex Pharmaceuticals, Inc., Waltham, Mass.

[ * ] Notice: This patent is subject to a terminal disclaimer.

[21] Appl. No.: 08/999,029

[22] Filed: Dec. 29, 1997

Related U.S. Application Data

[63] Continuation-in-part of application No. 08/659,264, Jun. 6, 1996, abandoned, application No. 08/482,969, Jun. 7, 1995, Pat. No. 5,703,188, application No. 08/779,779, Jan. 7, 1997, application No. 08/461,298, Jun. 5, 1995, Pat. No. 5,693,675, and application No. 08/910,692, Aug. 13, 1997, which is a division of application No. 08/460,980, Jun. 5, 1995, Pat. No. 5,679,717, which is a continuation-in-part of application No. 08/258,431, Jun. 10, 1994, abandoned, said application No. 08/659,264, is a continuation-in-part of application No. 08/469,659, Jun. 6, 1995, Pat. No. 5,618,530, which is a continuation-in-part of application No. 08/258,431, and application No. 08/332,096, Oct. 31, 1994, abandoned, said application No. 08/482,969, is a continuation-in-part of application No. 08/258,477, Jun. 10, 1994, Pat. No. 5,624,963, which is a continuation-in-part of application No. 08/071,564, Jun. 2, 1993, abandoned, said application No. 08/779,779, is a division of application No. 08/471,769, Jun. 6, 1995, Pat. No. 5,607,669, which is a continuation-in-part of application No. 08/258,431, and application No. 08/332,096, said application No. 08/461,298, is a continuation-in-part of application No. 08/258,431.

[51] Int. Cl.⁶ .............................. B01D 15/00; B01J 39/00
[52] U.S. Cl. ...................... 526/290; 526/293; 526/303.1; 526/307.2; 526/307.8; 526/310; 526/318.1; 526/326; 526/346; 514/789
[58] Field of Search ................................. 526/290, 293, 526/303.1, 307.2, 307.8, 310, 318.1, 326, 346; 514/789

[56] References Cited

U.S. PATENT DOCUMENTS

| | | | |
|---|---|---|---|
| 2,874,132 | 2/1959 | Riener . | |
| 3,288,770 | 11/1966 | Butler . | |
| 3,308,020 | 3/1967 | Wolf et al. | 167/65 |
| 3,383,281 | 5/1968 | Wolf et al. | 167/65 |
| 3,562,266 | 2/1971 | Minisci et al. . | |
| 3,692,895 | 9/1972 | Nelson et al. | 424/78 |
| 3,780,171 | 12/1973 | Irmscher et al. | 424/79 |
| 3,787,474 | 1/1974 | Daniels et al. . | |
| 3,801,641 | 4/1974 | Payot et al. . | |
| 3,803,237 | 4/1974 | Lednicer et al. . | |
| 3,980,770 | 9/1976 | Ingelman et al. | 424/79 |
| 4,027,009 | 5/1977 | Grier et al. | 424/78 |
| 4,071,478 | 1/1978 | Shen et al. . | |
| 4,098,726 | 7/1978 | Wagner et al. | 528/403 |
| 4,101,461 | 7/1978 | Strop et al. | 521/32 |
| 4,111,859 | 9/1978 | Strop et al. | 521/33 |
| 4,205,064 | 5/1980 | Wagner et al. | 424/78 |
| 4,217,429 | 8/1980 | Wagner et al. | 525/411 |
| 4,340,585 | 7/1982 | Borzatta et al. | 424/79 |

(List continued on next page.)

FOREIGN PATENT DOCUMENTS

| | | |
|---|---|---|
| 0 081 291 A3 | 6/1983 | European Pat. Off. . |
| 0 162 388 | 11/1985 | European Pat. Off. . |
| 0 323 847 A1 | 7/1989 | European Pat. Off. . |
| 0 373 852 A2 | 6/1990 | European Pat. Off. . |
| 0432995A1 | 6/1991 | European Pat. Off. . |
| 0 459 632 A1 | 12/1991 | European Pat. Off. . |
| 0 580 078 A1 | 1/1994 | European Pat. Off. . |
| 0 580 079 A1 | 1/1994 | European Pat. Off. . |
| 798488 | 7/1958 | United Kingdom . |
| 929391 | 6/1963 | United Kingdom . |
| 1567294 | 5/1980 | United Kingdom . |
| 2 090 605 | 7/1982 | United Kingdom . |
| WO91/18027 | 11/1991 | WIPO . |
| WO92/10522 | 6/1992 | WIPO . |
| WO94/04596 | 3/1994 | WIPO . |
| WO94/27620 | 12/1994 | WIPO . |
| WO 95/34585 | 12/1995 | WIPO . |
| WO 95/34588 | 12/1995 | WIPO . |
| WO 98/29107 | 9/1998 | WIPO . |

OTHER PUBLICATIONS

Heming, A.E. and Flanagan, Thomas L., "Considerations in the Selection of Cation Exchange Resins for Therapeutic Use," *Annals of the New York Academy of Sciences*, 57:239–251 (1954).

(List continued on next page.)

*Primary Examiner*—Nathan M. Nutter
*Attorney, Agent, or Firm*—Hamilton, Brook, Smith & Reynolds, P.C.

[57] ABSTRACT

The present invention relates to polymer compositions and methods of using said compositions for sequestering bile acids in a patient. The polymer compositions of this invention comprise a copolymer characterized by one or more hydrophilic nonamine-containing monomers or repeat units and one or more amine-containing monomers or repeat units. The amine-containing monomers or repeat units of the polymer compositions have one or more substituents bound to a portion of the amine nitrogens. The substituent or substituents which are bound to the amine nitrogens of the polymer composition can include a hydrophobic moiety and/or a quaternary amine-containing moiety. Suitable amine-containing monomers or repeat units include, but are not limited to, for example, vinylamine, allylamine, diallylamine, diallylmethylamine, and ethyleneimine, which are appropriately substituted, as described above.

The hydrophilic nonamine-containing monomer can be, but is not limited to, for example, allyl alcohol, vinyl alcohol, ethylene oxide, propylene oxide, hydroxyethylacrylate, hydroxyethylmethacrylate, hydroxypropylacrylate, hydroxypropylmethacrylate, poly(propyleneglycol) monomethacrylate, poly(ethyleneglycol) monomethacrylate, acrylic acid, carbon dioxide, and sulfur dioxide. Typically, the hydrophilic nonamine-containing monomer or repeat unit comprises from about 10 to about 90 mole percent of the polymer composition.

44 Claims, No Drawings

U.S. PATENT DOCUMENTS

| | | | |
|---|---|---|---|
| 4,426,489 | 1/1984 | Wessling et al. | 524/815 |
| 4,540,760 | 9/1985 | Harada et al. | 526/211 |
| 4,557,930 | 12/1985 | Kihara et al. | 424/79 |
| 4,559,391 | 12/1985 | Ueda et al. | 525/366 |
| 4,605,701 | 8/1986 | Harada et al. | 525/107 |
| 4,680,360 | 7/1987 | Ueda et al. | 526/310 |
| 4,759,923 | 7/1988 | Buntin et al. | 424/440 |
| 5,055,197 | 10/1991 | Albright et al. | 210/638 |
| 5,142,019 | 8/1992 | Sundararaman et al. | 528/271 |
| 5,189,111 | 2/1993 | Danner | 525/328.2 |
| 5,236,701 | 8/1993 | St. Pierre et al. | 424/78 |
| 5,300,566 | 4/1994 | Pinschmidt, Jr. et al. | 525/60 |
| 5,374,422 | 12/1994 | St. Pierre et al. | 424/78.12 |
| 5,395,896 | 3/1995 | Moriya et al. | 525/60 |
| 5,414,068 | 5/1995 | Bliem et al. | 528/288 |
| 5,428,112 | 6/1995 | Ahlers et al. | 525/326.7 |
| 5,430,110 | 7/1995 | Ahlers et al. | 525/328.2 |
| 5,451,397 | 9/1995 | Albright et al. | 424/78.01 |
| 5,462,730 | 10/1995 | McTaggart et al. | 424/78.35 |
| 5,500,212 | 3/1996 | Bliem et al. | 424/78.12 |
| 5,624,963 | 4/1997 | Mandeville, III et al. | 514/789 |

OTHER PUBLICATIONS

McCarthy, Peter A., "New Approaches to Atherosclerosis: An Overview," *Medicinal Research Reviews*, 13(2):139–159 (1993).

Butler, G.B. and Do, C.H., "Comblike Cyclopolymers of Alkyldiallylamines and Alkyldiallylmethylammonium Chlorides," in *Water–Soluble Polymers*, eds. Shalaby, McCormick & Butler, Chapter 9, pp. 151–158 ACS Symposium Series 467 (1991).

Dubin, P.L. and Davis, D.D., "Quasi–Elastic Light Scattering of Polyelectrolyte–Micelle Complexes," *Macromolecules 17*: 1294–1296 (1984).

Wang, G.–J. and Engberts, J., "Fluorescence probing of the formation of hydrophobic microdomains by cross–linked poly(alkylmethyldiallylammonium bromides) in aqueous solution," *Recl. Trav. Chim. Pays–Bas 113*:390–393 (1994).

Kunitake, T., et al., "Catalyses of Polymer Complexes. 4. Polysoap–Catalyzed Decarboxylation of 6–Nitrobenzisoxazole–3–carboxylate Anion. Importance of the Hydrophobic Environment in Activation of the Anion," *J. Org. Chem 42*(2): 306–312 (1977).

Wang, G.–J. and Engberts, J., "Study of the Conformational State of Non–Cross–Linked and Cross–Linked Poly(alkyl-methyldiallylammonium Chlorides) in Aqueous Solution by Fluorescence Probing," *Gazzetta Chimica Italiana*, 125: 393–397 (1995).

Kuron, G.W., et al., "The Bile Acid Binding and Hypocholesterolemic Action of Two Water–Soluble Polymers," *Atherosclerosis*, 37 353–360 (1980).

Harada, S. and Arai, K., "The Cyclo–copolymerization of Diallyl Compounds and Sulfur Dioxide," *Die Makromolekulare Chemie 107*: 64–93 (1967).

Wang, G.–J. and Engberts, J., "Induction of Aggregate Formation of Cationic Polysoaps and Surfactants by Low Concentrations of Additives in Aqueous Solution," *Langmuir*, 10(8): 2583–2587 (1994).

Wang, G.–J. and Engberts, J., "Synthesis of Hydrophobically and Electrostatically Modified Polyacrylamides and Their Catalytic Effects on the Unimolecular Decarboxylation of 6–Nitrobenzisoxazole–3–carboxylate Anion,"

Wang, G.–J. and Engberts, J., "Synthesis and Catalytic Properties of Non–Cross–Linked and Cross–Linked Poly-(alkylmethyldiallylammonium bromides) Having Decyl, Octyl, and Hexyl Side Chains," *J. Org. Chem*, 60: 4030–4038 (1995).

Kevelam, J., et al., "Polymer–Surfactant Interactions Studied by Titration Microcalorimetry: Influence of Polymer Hydrophobicity, Electrostatic Forces, and Surfactant Aggregational State," *Langmuir*, 12(20): 4709–4717 (1996).

Wang, G.–J. and Engberts, J., "Synthesis and Catalytic Properties of Cross–Linked Hydrophobically Associating Poly(alkylmethyldiallylammonium bromides)," *J. Org. Chem.*, 59(15): 4076–4081 (1994).

Yang, Y.J. and Engberts, J., "Synthesis and Catalytic Properties of Hydrophobically Modified Poly(alkylmethyldiallylammonium bromides)," *J. Org. Chem.*, 56: 4300–4304 (1991).

Negi, Y., et al., "Cyclopolymerization of Diallylamine Derivatives in Dimethyl Sulfoxide," *J. of Polymer Science: Part A–1*, 5: 1951–1965 (1967).

Hodgkin, H. et al., "Use of $^{13}$C–NMR in the Study of Reactions on Crosslinked Resins," Published by John Wiley & Sons, *J. of Polymer Science: Polymer Chemistry Edition*, 19(5): 1239–1249 (1981).

Yeh, F., et al., "Nanoscale Supramolecular Structures in the Gels of Poly(Diallyldimethylammonium Chloride) Interacting with Sodium Dodecyl Sulfate," *J. Am. Chem. Soc.*, 118(28): 6615–6618 (1996).

Boothe, J.E., et al., "Some Homo– and Copolymerization Studies of Dimethyldiallylammonium Chloride," *J. Macromol. Sci.–Chem.*, A4(6): 1419–1430 (1970).

United States Serial No. 08/777,408, filed on Dec. 30, 1996, "Poly(diallylamine)–Based Bile Acid Sequestrant" by Stephen Randall Holmes–Farley.

HYDROPHILIC NONAMINE-CONTAINING AND AMINE-CONTAINING COPOLYMERS AND THEIR USE AS BILE ACID SEQUESTRANTS

RELATED APPLICATIONS

This application is a Continuation-in-Part of U.S. application Ser. No. 08/659,264, filed Jun. 6, 1996, and now abandoned which is a Continuation-In-Part of application Ser. No. 08/469,659, filed Jun. 6, 1995, now U.S. Pat. No. 5,618,530 which is a Continuation-In-Part of applications having Ser. Nos. 08/258,431, filed Jun. 10, 1994 and 08/332,096, filed Oct. 31, 1994, both now abandoned. This application is also a Continuation-in-Part of application Ser. No. 08/482,969, filed Jun. 7, 1995, and now U.S. Pat. No. 5,703,188 which is a Continuation-in-Part of application Ser. No. 08/258,477, filed Jun. 10, 1994 now U.S. Pat. No. 5,624,963, which is a Continuation-In-Part of application Ser. No. 08/071,564, filed Jun. 2, 1993, now abandoned. This application is also a Continuation-in-Part of application Ser. No. 08/779,77 filed Jan. 7, 1997, which is a divisional of Ser. No. 08/471,769, filed Jun. 6, 1995, now U.S. Pat. No. 5,607,669 which is a Continuation-in-Part of applications having Ser. Nos. 08/258,431, filed Jun. 10, 1994, now abandoned and 08/332,096, filed Oct. 31, 1994 and now abandoned. This application is also a Continuation-in-Part of application Ser. No. 08/461,298, filed Jun. 5, 1995 and now U.S. Pat. No. 5,693,675 and 08/910,692 filed Aug. 13, 1997, which is a divisional of 08/460,980, filed Jun. 5, 1995, now U.S. Pat. No. 5,679,717. Applications having Ser. Nos. 08/461,298 and 08/460,980 are Continuation-In-Part applications of Ser. No. 08/258,431, now abandoned. The teachings of all of the above listed documents are incorporated herein by reference in their entirety.

BACKGROUND OF THE INVENTION

Biologically, cholesterol is eliminated from the body by conversion to bile acids and excretion as neutral steroids. Bile acids are synthesized from cholesterol in the liver and enter the bile as glycine and taurine conjugates. They are released in salt form in bile during digestion and act as detergents to solubilize and consequently aid in digestion of dietary fats. Following digestion, bile acid salts are mostly reabsorbed in the ileum, complexed with proteins, and returned to the liver through hepatic portal veins. The small amount of bile acid salts which are not reabsorbed by active transport are excreted via the distal ileum and large intestine as a portion of fecal material.

Therefore, reabsorption of bile acids, which can be present as the corresponding salts or conjugates, from the intestine conserves lipoprotein cholesterol in the bloodstream. As such, reducing reabsorption of bile acids within the intestinal tract can lower levels of bile acid circulating in the enterohepatic system thereby promoting replacement of bile acids through synthesis from cholesterol, in the liver. The result is a lowering of circulating blood cholesterol levels.

One method of reducing the amount of bile acids that are reabsorbed, is oral administration of compounds that sequester the bile acids within the intestinal tract and cannot themselves be absorbed. The sequestered bile acids consequently are excreted.

SUMMARY OF THE INVENTION

The present invention is based upon the discovery that polymer compositions which include copolymers characterized by one or more hydrophilic nonamine-containing monomers or repeat units and one or more amine-containing monomers or repeat units, as described herein, are as effective at sequestering bile acids in a patient as the corresponding amine-containing polymer alone.

The present invention relates to polymer compositions and methods of using said compositions for sequestering bile acids in a patient. The polymer compositions of this invention comprise a copolymer characterized by one or more hydrophilic nonamine-containing monomers or repeat units and one or more amine-containing monomers or repeat units. The amine-containing monomers or repeat units of the polymer compositions have one or more substituents bound to a portion of the amine nitrogens. The substituent or substituents which are bound to the amine nitrogens of the polymer composition include a hydrophobic moiety and/or a quaternary amine-containing moiety. As such, suitable substituents can include, for example, a hydrophobic moiety such as an alkyl group of at least six carbons, bound to an amine of the polymer, or, for example, a quaternary amine-containing moiety such as an alkyltrialkyl ammonium group bound to an amine of the polymer. It is to be understood that the quaternary amine-containing moiety and the hydrophobic moiety when employed in combination can be bound to the same and/or different amines of the polymer composition. In a specific embodiment, the quaternary amine-containing moiety can bear at least one terminal hydrophobic alkyl substituent, such as an alkyl group having between about six and twenty-four carbons, thereby providing both a hydrophobic and quaternary amine-containing moiety as a single substituent. Suitable amine-containing monomers or repeat units include, but are not limited to, for example, vinylamine, allylamine, diallylamine, alkyl diallylamine, vinyl imidazole, and ethyleneimine, which are appropriately substituted, as described above.

Further and more specific examples of amine-containing monomer or repeat unit components suitable for use in this invention, are described in U.S. Pat. Nos. 5,607,669, 5,618,530, 5,624,963 and 5,679,717 and copending U.S. Application having Ser. No. 08/659,264 filed on Jun. 6, 1996, the entire contents of which are incorporated herein by reference in their entirety. However, these amine-containing polymers can be difficult, costly and inefficient to prepare.

The hydrophilic nonamine-containing monomer can be organic or inorganic in nature. The nonamine-containing monomer can be, but is not limited to, for example, allyl alcohol, vinyl alcohol, ethylene oxide, propylene oxide, hydroxyethylacrylate, hydroxyethylmethacrylate, hydroxypropylacrylate, hydroxypropylmethacrylate, poly (propyleneglycol) monomethacrylate, poly(ethyleneglycol) monomethacrylate, acrylic acid, carbon dioxide, and sulfur dioxide. Typically, the nonamine-containing monomer or repeat unit comprises from about 25 to about 95 mole percent of the polymer composition, preferably from about 50 to 90 mole percent.

Methods of using the polymer compositions of the invention include their oral administration to a mammal in a therapeutically effective amount to sequester bile acids, reduce blood cholesterol, treat atherosclerosis, or treat hypercholesterolemia.

The polymer compositions of this invention have many unexpected advantages. That is, polymers characterized by the hydrophilic nonamine-containing monomers or repeat units of the invention, alone, although easy and inexpensive to prepare, are not known to exhibit bile acid sequestration properties. Therefore, it was unexpected that a polymer composition comprising a copolymer characterized by an amine-containing monomer or repeat unit and a hydrophilic nonamine-containing monomer or repeat unit, wherein a significant percentage of the composition is the nonamine-containing component, would possess bile acid sequestration properties similar to those exhibited by the corresponding substituted amine-containing polymer sequestrant alone. Since the nonamine-containing monomers are less expensive and polymerize more easily and efficiently than amine-containing monomers or repeat units, replacement of the amine-containing monomers or repeat units with nonamine-containing monomers or repeat units, in the preparation of the polymer compositions of the present invention, can reduce the cost and increase the availability of polymer compositions suitable for use as bile acid sequestrants.

Further, the hydrophilic nonamine-containing monomers can provide for increased binding strength of bile acids to the copolymer, despite the fact that they bind bile acids poorly or not at all when used alone. For example, certain functional groups, such as hydroxyl groups, can form hydrogen bonds to the hydroxyl groups present in bile acids. These hydrogen bonds can serve to increase the binding strength of bile acids to the copolymer compared to the binding in a homopolymer of the amine-containing monomer. Since increased binding strength is indicative of increased efficacy, these nonamine-containing monomers are contributing to efficacy despite their poor performance as bile acid sequestrants when used alone.

DETAILED DESCRIPTION OF THE INVENTION

The features and other details of the invention will now be more particularly described and pointed out below as well as in the claims. It will be understood that the particular embodiments of the invention are shown by way of illustration and not as limitations of the invention. The principle features of this invention can be employed in various embodiments without departing from the scope of the invention.

The present invention relates to polymer compositions and methods of using said compositions for sequestering bile acids in a patient. The polymer compositions of this invention, as defined herein, comprise a copolymer characterized by one or more hydrophilic nonamine-containing monomers or repeat units and one or more amine-containing monomers or repeat units. The amine-containing component has one or more substituents bound to a portion of the amine nitrogens. The substituent or substituents which are bound to a portion of the amine nitrogens of the polymer composition can include a hydrophobic moiety and/or a quaternary amine-containing moiety.

As used herein, the term, "amine-containing monomer," includes any monomer or repeat unit which, after polymerization and possible further reaction, will yield a polymer having a repeat unit characterized by an amine nitrogen wherein a portion of the amine nitrogens are substituted with a hydrophobic moiety and/or a quaternary amine-containing moiety. An "amine nitrogen" is defined as any nitrogen-containing moiety which has a positive charge under conditions present in the gastrointestinal tract. Suitable amine-containing monomers or repeat units include, but are not limited to, for example, suitably substituted vinylamine, allylamine, diallylamine, vinylimidazole, diallylmethylamine, and ethyleneimine. Other amine-containing monomers, suitable for use in the invention, include monomers which can be chemically altered by reactions such as hydrolysis, nucleophilic substitution and reduction to yield a polymer having a repeat unit or monomer characterized by an amine bearing a hydrophobic and/or a quaternary amine-containing moiety on a portion of the amine nitrogens. For example, polymerization of acrylamide gives poly(acrylamide) which can be reduced using reduction reactions well known in the art to give poly(allylamine). The poly(allylamine) can then be further modified by substituting a portion of the amine nitrogens with a hydrophobic moiety and/or a quaternary amine-containing moiety.

The substituent or substituents which are bound to the amine nitrogens of the amine-containing repeat unit of the polymer composition can include a hydrophobic and/or a quaternary amine-containing moiety. Suitable substituents can include, for example, a hydrophobic moiety such as an alkyl group of at least six carbons, bound to an amine of the polymer or, for example, a quaternary amine-containing moiety such as an alkyltrialkyl ammonium group bound to an amine of the polymer. In a specific embodiment, the quaternary amine-containing moiety can bear at least one terminal hydrophobic alkyl substituent, such as an alkyl group having between about six and twenty-four carbons, thereby providing both a hydrophobic and a quaternary amine-containing moiety as a single substituent. It is to be understood that multiple substituents can be bound to the same amine and/or different amines of the polymer composition.

A "hydrophobic moiety," as the term is used herein, is a moiety which, as a separate entity, is more soluble in octanol than water. For example, the octyl group ($C_8H_{17}$) is hydrophobic because its parent alkane, octane, has greater solubility in octanol than in water. The hydrophobic moieties can be a saturated or unsaturated, substituted or unsubstituted hydrocarbon group. Such groups include substituted and unsubstituted, normal, branched or cyclic alkyl groups having at least six carbon atoms, substituted or unsubstituted arylalkyl or heteroarylalkyl groups and substituted or unsubstituted aryl or heteroaryl groups. Preferably, the hydrophobic moiety includes an alkyl group of between about eight and twelve carbons. Specific examples of suitable hydrophobic moieties include the following alkyl groups n-hexyl, n-heptyl, n-octyl, n-nonyl, n-decyl, n-undecyl, n-dodecyl, n-tetradecyl, n-octadecyl, and combinations thereof. Other examples of suitable hydrophobic moieties include haloalkyl groups of at least six carbons (e.g., 10-halodecyl), hydroxyalkyl groups of at least six carbons (e.g., 11-hydroxyundecyl), and aralkyl groups (e.g., benzyl).

Suitable quaternary amine-containing moieties include alkyl trialkylammoniums also referred to as ammonioalkyl groups. The term, "ammonioalkyl," as used herein, refers to an alkyl group which is substituted by a nitrogen bearing three additional substituents. Thus, the nitrogen atom is an ammonium nitrogen atom which bears an alkylene substituent, which links the ammonium nitrogen atom to the nitrogen atom of the amine-containing monomer or repeat unit, and three additional terminal alkyl substituents having from about one to about twenty-four carbons. A "terminal substituent" of the quaternary amine, as the term is employed herein, is any one of the three substituents on the quaternary amine nitrogen which is not the carbon chain between the amine on the polymer backbone and the amine of the quaternary ammonium center.

An ammonioalkyl group will further include a negatively charged counterion, such as a conjugate base of a pharmaceutically acceptable acid. Examples of suitable counterions include $Cl^-$, $Br^-$, $CH_3SO_3^-$, $HSO_4^-$, $SO_4^{2-}$, $HCO_3^-$, $CO_3^{2-}$, acetate, lactate, succinate, propionate, butyrate, ascorbate, citrate, maleate, folate, an amino acid derivative, and a nucleotide.

Suitable ammonioalkyl groups are of the general formula:

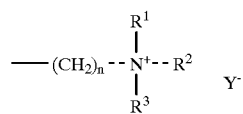

(I)

wherein, $R^1$, $R^2$ and $R^3$ represent an alkyl group, wherein each R, independently, is a normal or branched, substituted or unsubstituted alkyl group having a carbon atom chain length of between about one to about twenty-four carbon atoms, n is an integer having a value of three or more and Y is a negatively charged counterion. In a particular embodiment, $R^1$, $R^2$ and $R^3$ are all methyl groups and n is an integer between about 3 and about 12 (e.g., 3, 4, 5, 6, 7, 8, 9, 10, 11, or 12).

The alkyl group, which provides the alkylene linking group between the amine of the amine-containing monomer or repeat unit and the ammonium nitrogen of the alkyl trialkylammonium group is three or more carbon atoms in length. Examples of preferred alkylene linking groups are propyl, butyl, pentyl, hexyl, octyl, and decyl groups. Example of suitable quaternary amine-containing moieties include, but are not limited to:
4-(trimethylammonio)butyl;
6-(trimethylammonio)hexyl;
8-(trimethylammonio)octyl;
10-(trimethylammonio)decyl;
12-(trimethylammonio)dodecyl and combinations thereof. A particularly preferred amine-containing moiety is a 6-(trimethylammonio)hexyl group.

Alternatively, a quaternary amine-containing moiety and a hydrophobic moiety are present in the same substituent. For example, the quaternary amine nitrogen or ammonium nitrogen of the quaternary amine-containing moiety is bound to the amine of the polymer backbone by an alkylene having three or more carbons. However, at least one of the three terminal substituents ($R^1$, $R^2$ and $R^3$) of the ammonium nitrogen is a hydrophobic alkyl group having from six to about twenty-four carbons. The remaining terminal substituents are each independently a normal or branched, substituted or unsubstituted alkyl group having from one to about twenty-four carbons. In another embodiment, at least two of the three terminal substituents can be hydrophobic alkyl groups having from six to about twenty-four carbons the remainder having from one to about twenty-four carbons. In a further embodiment, all three of the terminal substituents can be hydrophobic alkyl groups having from six to about twenty-four carbons.

A "hydrophobic alkyl group," as that term is employed herein, includes a substituted or unsubstituted alkyl group having from six to about twenty-four carbons and which is hydrophobic, as earlier defined. The hydrophobic alkyl group can be, for example, a normal or branched, substituted or unsubstituted alkyl group having from six to about twenty-four carbons.

Particular examples of quaternary amine-containing moieties, which provide both a hydrophobic and quaternary amine-containing substituent, include, but are not limited to:
4-(dioctylmethylammonio)butyl;
3-(dodecyldimethylammonio)propyl;
3-(octyldimethylammonio)propyl;
3-(decyldimethylammonio)propyl;
5-(dodecyldimethylammonio)pentyl;
3-(dimethyldecylammonio)hexyl;
6-(decyldimethylammonio)hexyl;
3-(tridecylammonio)propyl;
3-(docosyldimethylammonio)propyl;
6-(docosyldimethylammonio)hexyl;
4-(dodecyldimethylammonio)butyl;
3-(octadecyldimethylammonio)propyl;
3-(hexyldimethylammonio)propyl;
3-(methyldioctylammonio)propyl;
3-(didecylmethylammonio)propyl;
3-(heptyldimethylammonio)propyl;
3-(dimethylnonylammonio)propyl;
6-(dimethylundecylammonio)hexyl;
4-(heptyldimethylammonio)butyl;
4-(dioctylmethylammonio)butyl;
6-(octyldimethylammonio)hexyl;
12-(decyldimethylammonio)dodecyl;
3-(dimethylundecylammnio)propyl; and
3-(tetradecyldimethylammonio)propyl.

The polymer composition of the invention which includes alkylated amines can be formed, for example, by reacting a polymer, which can be linear or crosslinked, with a suitable alkylating agent or by polymerizing an alkylated monomer.

An "alkylating agent," as that term is employed herein, means a reactant that, when reacted with an amine-containing monomer or a copolymer characterized by an amine-containing repeat unit of the invention, causes a substituent, as described herein, to be covalently bound to one or more of the amine nitrogen atoms of the monomer or copolymer. It is to be understood that under these conditions, hydroxyls contained in the polymer compositions can also react with alkylating agents. Further, when multiple substituents are employed, they can be bound to the same and/or different amine nitrogens.

Suitable alkylating agents are compounds comprising an alkyl group or alkyl derivative, having at least six carbon atoms, which is bonded to a leaving group such as a halo (e.g., chloro, bromo or iodo), tosylate, mesylate or epoxy group.

Examples of suitable alkylating agents which provide a hydrophobic moiety include alkyl halides having at least six carbon atoms, such as n-hexyl halide, n-heptyl halide, n-octyl halide, n-nonyl halide, n-decyl halide, n-undecyl halide, n-dodecyl halide, n-tetradecyl halide, n-octadecyl halide, and combinations thereof. Other examples include: a dihaloalkane that includes an alkyl group of at least six carbons (e.g., a 1,10-dihalodecane); a hydroxyalkyl halide having at least six carbon atoms (e.g., an 11-halo-1-undecanol); an aralkyl halide (e.g., a benzyl halide); an alkyl epoxy ammonium salt having at least six carbons (e.g., glycidylpropyl-trimethylammonium salts) and epoxyalkylamides having at least six carbons (e.g., N-(2,3-epoxypropyl) butyramide or N-(2,3-epoxypropyl) hexanamide).

Preferred halogen components of the alkyl halides are bromine and chlorine. Particularly preferred alkylating agents which, when reacted with the polymer composition, will cause formation of an amine polymer reaction product that includes a first substituent, are 1-bromodecane and 1-chlorodecane.

Examples of suitable alkylating agents which can provide a quaternary amine-containing moiety have the general formula:

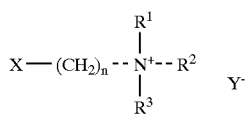

wherein,

R$^1$, R$^2$, and R$^3$ represent an alkyl group, wherein each R independently, is a normal or branched, substituted or unsubstituted alkyl group having a carbon atom chain length of between about one to about twenty four carbon atoms, n is an integer having a value of three or more, X is a leaving group as earlier described, and Y is a negatively charged counterion.

When at least one of the three terminal substituents of the quaternary amine alkylating agent is a hydrophobic alkyl group having from six to about twenty-four carbons, the alkylating agent therefore provides both a hydrophobic moiety and a quaternary amine-containing moiety. The alkylene group in this instance is three or more carbon atoms in length.

Particular examples of quaternary ammonium compounds suitable as alkylating agents include the following:
(4-bromobutyl)dioctylmethylammonium bromide;
(3-bromopropyl)dodecyldimethylammonium bromide;
(3-chloropropyl)dodecyldimethylammonium bromide;
(3-chloropropyl) decyldimethylammonium bromide;
(5-tosylpentyl)dodecyldimethylammonium bromide;
(6-bromohexyl)dimethyldecylammonium bromide
(12-bromododecyl)decyldimethylammonium bromide;
(3-bromopropyl)tridecylammonium bromide;
(3-bromopropyl)docosyldimethylammonium bromide;
(6-bromohexyl)docosyldimethylammonium bromide;
(4-chlorobutyl)dodecyldimethylammonium bromide;
(3-chloropropyl)octadecyldimethylammonium bromide;
(3-bromopropyl)octyldimethylammonium bromide;
(3-iodobutyl)dioctylmethylammonium bromide;
(2,3-epoxy propyl)decyldimethylammonium bromide; and
(3-bromohexyl)docosyldimethyammonium bromide Examples of suitable alkyl trimethylammonium alkylating agents include alkyl halide trimethylammonium salts, such as:
(4-halobutyl)trimethylammonium salt;
(5-halopentyl)trimethylammonium salt;
(6-halohexyl)trimethylammonium salt;
(7-haloheptyl)trimethylammonium salt;
(8-halooctyl)trimethylammonium salt;
(9-halononyl)trimethylammonium salt;
(10-halodecyl) trimethylammonium salt;
(11-haloundecyl)trimethylammonium salt;
(12-halododecyl)trimethylammonium salt; and combinations thereof. A particularly preferred quaternary amine-containing alkylating agent is (6-bromohexyl) trimethylammonium bromide.

In one embodiment, the polymer composition of the invention is prepared by alkylating a copolymer characterized by an amine-containing monomer which is not substituted and a nonamine-containing monomer. Alkylation is accomplished by combining the copolymer with one or more alkylating agents, simultaneously or sequentially in any order. The copolymer can be optionally crosslinked. The total amount of the alkylating agent or alkylating agents combined with the polymer composition is generally sufficient to cause reaction of the alkylating agent or alkylating agents with between about 10 and 100 percent of amine groups on the polymer composition. Preferably the range is between about 50 and 100 percent. In a particularly preferred embodiment, the range is between about 75 and 100 percent. Examples of suitable solvents include, for example, but are not limited to, methanol, ethanol, isopropanol, acetonitrile, water, and mixtures thereof. Preferred solvents are methanol and water.

In a specific embodiment, a hydrophobic moiety is introduced by alkylation with 1-bromodecane. In another embodiment, a quaternary amine-containing moiety is introduced by alkylation with (6-bromohexyl) trimethylammonium bromide.

In the embodiment wherein one substituent includes both a quaternary amine-containing moiety and a hydrophobic moiety, as a terminal substituent on the quaternary amine nitrogen, preferred alkylating agents include (3-chloropropyl)dodecyldimethylammonium bromide and (4-chlorobutyl)dioctylmethylammonium bromide.

In one embodiment, the reaction mixture of unsubstituted copolymer and at least one alkylating agent is heated over a period of about forty minutes to a temperature of about 65° C., with stirring. Typically, an aqueous sodium hydroxide solution is intermittently added during the reaction period. Preferably, the reaction period at 65° C. is about eighteen hours, followed by gradual cooling to a room temperature of about 25° C. over a period of about four hours. The resulting reaction product is then filtered, resuspended in methanol, filtered again, and then washed with a suitable aqueous solution, such as two molar sodium chloride, and then with deionized water. The resultant solid product is then dried under suitable conditions, such as at a temperature of about 60° C. in a forced-air oven. The dried solid can then be subsequently processed. Preferably, the solid is ground and passed through an 80 mesh sieve.

The term, "hydrophilic nonamine-containing monomer or repeat unit," refers to any monomer which after polymerization and possible further reaction will yield a polymer having a repeat unit or monomer which does not contain a nitrogen atom and which is a hydrophilic moiety. A hydrophilic moiety, as the term is used herein, is a moiety which, as a separate entity, has a log P value less than 1.0, where P is the partition coefficient of the entity between octanol and water. (See, for example, *Exploring QSAR, Fundamentals and Applications in Chemistry and Biology,* by Corwin Hansch and Albert Leo, 1995, American Chemical Society.)

Suitable hydrophilic nonamine-containing monomers include, for example, allyl alcohol, vinyl alcohol, ethylene oxide, propylene oxide, substituted and unsubstituted acrylates and methacrylates, such as hydroxyethylacrylate, hydroxyethylmethacrylate, hydroxypropylacrylate, hydroxypropylmethacrylate, poly(propyleneglycol) monomethacrylate, and poly(ethyleneglycol) monomethacrylate, acrylic acid, carbon dioxide, and sulfur dioxide. In copolymers comprising sulfur dioxide, the polymer backbone includes —SO$_2$— units between pairs of amine-containing monomers or repeat units.

Examples of suitable methods by which polymer compositions can be formed are described below:

1. One method involves copolymerizing an amine monomer, such as vinyl amine, allylamine or ethyleneimine, with one or more additional monomers. These additional monomers can include other amine monomers, such as those listed above, as long as a non-amine monomer is present. Suitable nonamine-containing monomers include, but are not limited to, allyl alcohol, vinyl alcohol, ethylene oxide, propylene oxide, substituted and unsubstituted acrylates, and methacrylates, such as hydroxyethylacrylate, hydroxyethylmethacrylate, hydroxypropylacrylate, hydroxypropylmethacrylate, poly(propyleneglycol) monomethacrylate, and poly(ethyleneglycol) monomethacrylate, acrylic acid, carbon dioxide, and sulfur dioxide. Examples of suitable copolymers can include copoly(allylamine/vinyl alcohol), copoly(vinylamine/vinyl alcohol), and copoly(ethyleneimine/allyl alcohol).

The copolymer is then alkylated as described above to give the polymer composition of the invention wherein one or more substituents are bound to an amine of the copolymer and provide at least one hydrophobic moiety and one quaternary amine-containing moiety.

Alternatively, the amine monomers are alkylated with the desired substituent(s) prior to polymerization. In addition, preparation of the polymer composition of the invention can include alkylation of the amine containing-monomer both prior to and subsequent to polymerization. For example, the amine-containing monomer or repeat unit can be alkylated with, for example, a substituent having a quaternary amine-containing moiety. This monomer is then copolymerized with the nonamine-containing monomer, and optionally alkylated again with, for example, a substituent having a hydrophobic moiety.

Polymerization can be accomplished using techniques known in the art of polymer synthesis. (See, for example, Shalaby et al., ed., *Water-Soluble Polymers,* American Chemical Society, Washington, D.C. [1991]). The appropriate monomers can be polymerized by methods known in the art, for example, via a free radical addition process. In this case the polymerization mixture includes a free-radical initiator. Suitable free-radical initiators include azobis (isobutyronitrile), azobis(4-cyanovaleric acid), azobis (amidinopropane dihydrochloride), potassium persulfate, ammonium persulfate, and potassium hydrogen persulfate. Other suitable initiators include ionizing radiation and ultraviolet light. The free radical initiator is preferably present in the reaction mixture in an amount ranging from about 0.1 mole percent to about 5 mole percent relative to the monomer.

The polymer composition can be linear or crosslinked. Crosslinking can be performed by reacting the copolymer with one or more crosslinking agents having two or more functional groups, such as electrophilic groups, which react with amine groups to form a covalent bond. Crosslinking in this case can occur, for example, via nucleophilic attack of the polymer amino groups on the electrophilic groups. This results in the formation of a bridging unit which links two or more amino nitrogen atoms from different polymer strands. Suitable crosslinking agents of this type include compounds having two or more groups selected from among acyl chloride, epoxide, and alkyl-X, wherein X is a suitable leaving group, such as a halo, tosyl or mesyl group. Examples of such compounds include, but are not limited to, epichlorohydrin, succinyl dichloride, acryloyl chloride, butanedioldiglycidyl ether, ethanedioldiglycidyl ether, pyromellitic dianhydride, and dihaloalkanes.

The polymer composition can also be crosslinked by including a multifunctional co-monomer as the crosslinking agent in the reaction mixture. A multifunctional co-monomer can be incorporated into two or more growing polymer chains, thereby crosslinking the chains. Suitable multifunctional co-monomers include, but are not limited to, diacrylates, triacrylates, and tetraacrylates, dimethacrylates, diacrylamides, diallylacrylamides, and dimethacrylamides. Specific examples include ethylene glycol diacrylate, propylene glycol diacrylate, butylene glycol diacrylate, ethyl-ene glycol dimethacrylate, butylene glycol dimethacrylate, methylene bis(methacrylamide), ethylene bis(acrylamide), ethylene bis(methacrylamide), ethylidene bis(acrylamide), ethylidene bis(methacrylamide), pentaerythritol tetraacrylate, trimethylolpropane triacrylate, bisphenol A dimethacrylate, and bisphenol A diacrylate. Other suitable multifunctional monomers include polyvinylarenes, such as divinylbenzene.

The polymer compositions are preferably crosslinked prior to alkylation. The amount of crosslinking agent is typically between 0.5 and 25 weight %, based upon combined weight of crosslinking agent and monomer, with 2.5–20%, or 1–10, being preferred. Typically, the amount of crosslinking agent that is reacted with the polymer composition is sufficient to cause between about 0.1 and twenty percent of the amines to react with the crosslinking agent. In a preferred embodiment, between about 5 and 15 percent of the amine groups react with the crosslinking agent. It is to be understood that under these conditions, hydroxyls contained in the polymer compositions can also react with the crosslinking agent.

Crosslinking of the polymer composition can be achieved by reacting the copolymer with a suitable crosslinking agent in an aqueous caustic solution at about 25° C. for a period of time of about eighteen hours to thereby form a gel. The gel is then combined with water and blended to form a particulate solid. The particulate solid can then be washed with water and dried under suitable conditions, such as a temperature of about 50° C. for a period of time of about eighteen hours.

2. A second method involves copolymerizing monomers wherein the resulting copolymer contains functional groups which can be chemically modified to provide the nonamine-containing and amine containing repeat units which characterize the polymer composition of the invention. For example, acrylamide and vinyl acetate can be copolymerized. The copolymer can then be subjected to a reduction reaction such that the acrylamide is reduced to allylamine and vinyl acetate is reduced to vinyl alcohol, thereby providing copoly(allylamine/vinyl alcohol).

In another embodiment, acrylonitrile and vinyl acetate can be copolymerized followed by reduction and hydrolysis also providing copoly(allylamine/vinyl alcohol). It is to be understood that not all of the initial monomers are chemically altered, resulting in a polymer composition that contains some of the initial monomers.

As described above, alkylation to obtain the polymer composition of the invention can be performed prior to and/or subsequent to polymerization. In addition, the polymer composition can be linear or crosslinked. Crosslinking can be performed either prior to or subsequent to alkylation. Preferably, crosslinking is performed prior to alkylation.

Each of the polymer compositions of the present invention typically have a molecular weight greater than about 2,000. Examples of suitable polymer compositions include copoly(allylamine/vinyl alcohol), copoly(vinylamine/vinyl alcohol), and copoly(ethyleneimine/allyl alcohol) bearing one or more substituents having a hydrophobic or quaternary amine-containing moiety. A preferred polymer composition includes the copolymer copoly(vinylamine/vinyl alcohol).

The polymer compositions of the invention can have a wide range of compositions. Typically the amine-containing monomer or repeat unit will be present at from about 5 to about 75 mole percent of the polymer composition, preferably from about 10 to 50 percent.

The polymer composition of the invention comprises a copolymer characterized by one or more hydrophilic nonamine-containing monomers and one or more amine-containing monomers wherein one or more substituents are bound to the amine nitrogens of the copolymer. The substituents can include a hydrophobic moiety and/or a quaternary amine-containing moiety.

In preferred embodiments, the polymer composition of the invention is crosslinked and the amine-containing repeat unit is vinylamine, allylamine, diallylamine, alkyl diallylamine, vinyl imidazole, or ethyleneimine, having one or more substituents which can include a hydrophobic moiety and/or a quaternary amine-containing moiety, bound to the amine nitrogens. In specific embodiments, the substituent provides a hydrophobic moiety and is an alkyl group of at least six carbons. In a preferred embodiment, the alkyl group is between about eight and twelve carbons. In a particularly preferred embodiment, the alkyl group is about ten carbons.

In further specific embodiments, the substituent provides a quaternary amine-containing moiety and is an alkyl trimethylammonium group. In a preferred embodiment, the alkyl group of the alkyl trimethylammonium group is between about two and about twelve carbons. In particularly preferred embodiments the alkyl group is a hexyl, octyl or decyl group.

In yet another embodiment a single substituent provides both a hydrophobic and a quaternary amine-containing moiety. In preferred embodiments, the single substituent can include 3-(dodecyldimethylammonio)propyl and 4-(dioctylmethylammonio)butyl.

In a particularly preferred embodiment of the invention, the polymer composition is a crosslinked copoly (vinylamine/vinyl alcohol) polymer, wherein a substituent which provides a hydrophobic moiety is a decyl group, and is present in combination with a substituent which provides a quaternary amine-containing moiety which is 6-(trimethylammonio)hexyl.

The polymer compositions of the invention are non-toxic and stable when ingested. By "non-toxic" it is meant that when ingested in therapeutically effective amounts neither the reaction products nor any ions released into the body upon ion exchange are harmful. The high molecular weight and/or water-insolubility of the polymer renders the polymer substantially resistant to absorption. When the polymer is administered as a salt, the cationic counterions are preferably selected to minimize adverse effects on the patient, as is more particularly described below.

By "stable" it is meant that when ingested in therapeutically effective amounts the reaction products do not dissolve or otherwise decompose in vivo to form potentially harmful by-products, and remain substantially intact so that they can transport material out of the body.

The polymer compositions can be present as salts. By "salt" it is meant that the nitrogen group in the repeat unit is protonated or alkylated to create a positively charged nitrogen atom associated with a negatively charged counterion. Examples of suitable counterions include $Cl^-$, $Br^-$, $CH_3SO_3^-$, $HSO_4^-$, $SO_4^{2-}$, $HCO_3^-$, $CO_3^-$, acetate, lactate, succinate, propionate, butyrate, ascorbate, citrate, maleate, folate, an amino acid derivative, or a nucleotide.

Methods of use of the polymer compositions of the invention include their oral administration to a mammal in a therapeutically effective amount to bind bile salts, reduce blood cholesterol, treat atherosclerosis, treat hypercholesterolemia, or reduce plasma lipid content of the mammal. Generally, a therapeutic amount of the polymer composition, is an amount in a range of from about 1 mg/kg/day to about 10 g/kg/day, preferably between about 1 mg/kg/day to about 200 mg/kg/day.

In one embodiment, the method of the invention is a method for binding bile salts in a mammal, comprising the step of orally administering to the mammal a therapeutically effective amount of a polymer composition of the invention.

In another embodiment, the invention is a method for reducing blood cholesterol in a mammal, comprising the step of administering to the mammal a therapeutically effective amount of a polymer composition, of the invention. In still another embodiment, the invention includes a method for treating atherosclerosis in a mammal, comprising the step of administering to the mammal a therapeutic amount of a polymer composition of the invention, preferably a copoly (vinylamine/vinyl alcohol) polymer, of the invention.

In still another embodiment, the method of the invention is that of treating hypercholesterolemia in a mammal, comprising the step of administering to the mammal a therapeutically effective amount of a polymer composition of the invention, preferably a copoly(vinylamine/vinyl alcohol) polymer composition of the invention.

As used herein, the term, "therapeutically effective amount," refers to an amount which is sufficient to bind bile salts, reduce blood cholesterol, treat atherosclerosis, or treat hypercholesterolemia.

The polymer compositions may have fixed positive charges, or may have the capability of becoming charged upon ingestion at physiological pH. In the latter case, the charged ions also pick up negatively charged counterions upon ingestion that can be exchanged with bile salts. In the case of polymer compositions having fixed positive charges, however, the reaction product can be provided with one or more exchangeable counterions. Examples of suitable counterions include $Cl^-$, $Br^-$, $CH_3SO_3^-$, $HSO_4^-$, $SO_4^{2-}$, $HCO_3^-$, $CO_3^-$, acetate, lactate, succinate, propionate, butyrate, ascorbate, citrate, maleate, folate, an amino acid derivative, or a nucleotide. The counterions may be the same as, or different from, each other. For example, the amine polymer composition can contain two different types of counterions, both of which are exchanged for the bile salts being removed. More than one polymer composition, each having different counterions associated with the fixed charges, can be administered as well.

The polymer compositions of the invention can be subsequently treated or combined with other materials to form compositions for oral administration of the polymer compositions.

The present pharmaceutical compositions are generally prepared by known procedures using well known and readily available ingredients. In making the copolymer compositions of the present invention, the polymer composition can be present alone, can by admixed with a carrier, diluted by a carrier, or enclosed within a carrier which may be in the form of a capsule, sachet, paper or other container. When the carrier serves as a diluent, it can be a solid, semi-solid or liquid material which acts as a vehicle, excipient or medium for the polymer. Thus, the compositions can be in the form of tablets, pills, powders, lozenges, sachets, cachets, elixirs, suspensions, syrups, aerosols, (as a solid or in a liquid medium), soft or hard gelatin capsules, sterile packaged powders, and the like. Examples of suitable carriers, excipients, and diluents include foods, drinks, lactose, dextrose, sucrose, sorbitol, mannitol, starches, gum acacia, alginates, tragacanth, gelatin, calcium silicate, microcrystalline cellulose, polyvinylpyrrolidone, cellulose, methyl cellulose, methylhydroxybenzoates, propylhydroxybenzoates, and talc.

The invention will now be further and specifically described by the following examples. All parts and percentages are by weight unless otherwise specified.

EXEMPLIFICATION

Synthetic Methods

Example 1

To a 1-L beaker was added vinylamine/vinyl alcohol copolymer (62.5 g; mw=39,700; 12% vinylamine free base, 88% vinylalcohol) and water (187.5 g). The mixture was heated on a water bath with stirring until a creamy mixture was obtained. Methanol (250 mL) was added, followed by epichlorohydrin (2.8 g). The mixture was stirred at room temperature until it gelled and was then allowed to cure for 18 h. The gel was broken up, suspended in water (5 L), stirred for 30 minutes, and the solid gel was collected by filtration. The solid was dried in a forced air oven at 60° C. for 5 days to yield 58.9 g of white solid. The dried solid was ground and passed through a 10 mesh sieve.

The sieved solid (14.8 g) was suspended in water (750 mL) along with aqueous sodium hydroxide (1.5 g of 50% solution) and (3-chloropropyl)dodecyldimethylammonium bromide (70 g). The mixture was heated to reflux and an additional total of 13.5 g of 50% aqueous sodium hydroxide was added in nine equal portions at 45 minute intervals. The heating was continued for a total of 24 hours, followed by cooling to room temperature. Concentrated hydrochloric acid (50 mL) was added, the mixture was stirred for 30 minutes, and the solid was collected by filtration. The solid was washed in the funnel with methanol (1.5 L). The solid was then washed by suspension, agitation for 30 minutes, and collection by filtration using the following solvents:
1. Methanol (1 L)
2. 2 M NaCl (1.7 L)
3. 2 M NaCl (1.7 L)
4. 2 M NaCl (1.7 L)

The solid was washed on the funnel with water (4 L) and then rinsed as above in water (1 L) containing concentrated hydrochloric acid (2.0 mL). The solids were collected by filtration and dried in a forced air oven at 60° C. for 24 h to yield 15.7 g of product.

Example 2

Polyvinylamine free base (mw=40,000; Air Products; 62.5 g) was dissolved in water (188 mL) and methanol (250 mL). Epichlorohydrin (2.8 g) was added and the mixture stirred until it gelled. The gel was broken up and suspended in water (13 L). The solid was collected by filtration and dried in a forced air oven at 60° C. to yield 75.2 g of solid. This solid was ground and passed through a 10 mesh sieve.

The ground solid (14.8 g) was reacted in a manner similar to example 1, using 140 g of (3-chloropropyl) dimethyldodecylammonium bromide and 30 g of aqueous base, yielding 57.7 g of product.

In Vivo Testing

Example 3

The cholesterol lowering agents made in Example 1 and Example 2 were tested in vivo in hamsters in two different models.

In the first model, hamsters were acclimated to the laboratory for 1 week, then fed a high fat diet for an additional 6 days. At the end of this time the test hamsters received the same food supplemented with 0.3% by weight of polymer composition, while the control hamsters were maintained on the original diet. The test diets were continued for 2 weeks, during which time the cholesterol levels of the control hamsters became elevated. In comparison, the hamsters fed the diet which contained the cholesterol lowering agents did not rise significantly, or even decreased. Blood samples were then drawn and the total cholesterol levels were determined. The reported error ranges indicate ±1 standard deviation.

| Example | Total Cholesterol | Dose (% in diet) |
| --- | --- | --- |
| Control (no polymer) | 319 ± 37 mg/dL | 0 |
| 1 | 92 ± 7 | 0.30 |
| 2 | 97 ± 9 | 0.30 |
| Cholestyramine | 161 ± 57 | 1.20 |

From this experiment it is apparent that the polymer compositions of Examples 1 and 2 are potent cholesterol lowering agents. For comparison purposes, the commercial drug, cholestyramine, was also tested in the same hamster model, and it was found that at 4 times the dose (1.2% by weight in the diet) it had diminished cholesterol lowering activity as compared to the polymer compositions of Examples 1 and 2. Thus, the polymer compositions of Examples 1 and 2 possess similar activity and are highly potent cholesterol lowering agents.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

We claim:

1. A method for removing bile salts from a patient comprising administering to said patient a therapeutically effective amount of a polymer composition comprising a copolymer characterized by:

(1) one or more hydrophilic non-amine containing monomers; and (2) one or more amine-containing monomers wherein one or more substituents are bound to a portion of the amine nitrogens, and include a hydrophobic moiety and/or a quaternary amine-containing moiety.

2. The method of claim 1, wherein the amine-containing monomer is selected from the group consisting of: allylamine, diallylamine, diallylmethylamine, vinylamine, and ethyleneimine.

3. The method of claim 1 wherein said hydrophilic non-amine containing monomer is selected from the group consisting of allyl alcohol, vinyl alcohol, ethylene oxide, propylene oxide, hydroxyethylacrylate, hydroxypropylmethacrylate, poly(propyleneglycol) monomethacrylate, and poly(ethyleneglycol) monomethacrylate, acrylic acid, carbon dioxide, and sulfur dioxide.

4. The method of claim 1 wherein said polymer composition comprises one or more exchangeable counterions.

5. The method of claim 4 wherein at least one of said counterions is $Cl^-$, $Br^-$, $CH_3SO_3^-$, $HSO_4^-$, $SO_4^{2-}$, $HCO_3^-$, $CO_3^{2-}$, acetate, lactate, succinate, propionate, butyrate, ascorbate, citrate, maleate, folate, an amino acid derivative, or a nucleotide.

6. The method of claim 1 wherein said hydrophobic moiety is a substituted or unsubstituted, normal, branched or cyclic alkyl group having at least six carbon atoms.

7. The method of claim 6, wherein the hydrophobic moiety is an alkyl group of between about eight and twelve carbons.

8. The method of claim 6 wherein the hydrophobic moiety is an alkyl group of about ten carbons.

9. The method of claim 1 wherein the copolymer is crosslinked.

10. The method of claim 9 wherein the copolymer is crosslinked prior to substitution of the amine nitrogens.

11. The method of claim 9 wherein said polymer composition is crosslinked by means of a multifunctional crosslinking co-monomer, said co-monomer being present in an amount from about 0.5% to about 25% by weight, based upon total monomer weight.

12. The method of claim 11 wherein said crosslinking co-monomer is present in an amount from about 1% to about 10% by weight, based upon total monomer weight.

13. The method of claim 1, wherein the quaternary amine-containing moiety has the following formula:

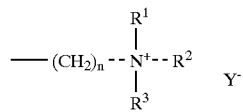

wherein,
R$^1$, R$^2$ and R$^3$ represent an alkyl group, wherein each R, independently, is a normal or branched, substituted or unsubstituted alkyl group having a carbon atom chain length of between about one to about twenty four carbon atoms,
n is an integer having a value of three or more, and
Y is a negatively-charged counterion.

14. The method of claim 13, wherein R$^1$, R$^2$ and R$^3$ are all methyl groups and n has a value between about three and about twelve carbons.

15. The method of claim 14, wherein n is 6.

16. The method of claim 14, wherein n is 8.

17. The method of claim 14, wherein n is 10.

18. The method of claim 13 wherein at least one of R$^1$, R$^2$ and R$^3$ is a hydrophobic alkyl group having from six to about twenty-four carbons the remainder of which each independently having from one to twenty-four carbons.

19. The method of claim 18 wherein the quaternary amine-containing moiety is 3-(dodecyldimethylammonio) propyl.

20. The method of claim 13 wherein at least two of R$^1$, R$^2$ and R$^3$ are hydrophobic alkyl groups having from six to about twenty-four carbons the remainder having from one to twenty-four carbons.

21. The method of claim 20 wherein the quaternary amine-containing moiety is 4-(dioctylmethylammonio) butyl.

22. The method of claim 13 wherein all three of R$^1$, R$^2$ and R$^3$ are hydrophobic alkyl groups having from six to about twenty-four carbons.

23. A polymer composition comprising a copolymer characterized by:
(1) one or more a hydrophilic non-amine containing monomers; and
(2) one or more amine-containing monomers wherein one or more substituents are bound to a portion of the amine nitrogens, and include a hydrophobic moiety and/or a quaternary amine-containing moiety.

24. The polymer composition of claim 23, wherein the amine-containing monomer is selected from the group consisting of: allylamine, vinylamine, diallylamine, diallylmethylamine, and ethyleneimine.

25. The polymer composition of claim 23 wherein said hydrophilic non-amine containing monomer is selected from the group consisting of allyl alcohol, vinyl alcohol, ethylene oxide, propylene oxide, hydroxyethylacrylate, hydroxyethylmethacrylate, hydroxypropylacrylate, hydroxypropylmethacrylate, poly(propyleneglycol) monomethacrylate, and poly(ethyleneglycol) monomethacrylate, acrylic acid, carbon dioxide, and sulfur dioxide.

26. The polymer composition of claim 23 wherein said polymer composition comprises one or more exchangeable counterions.

27. The polymer composition of claim 26 wherein at least one of said counterions is Cl$^-$, Br$^-$, CH$_3$SO$_3^-$, HSO$_4^-$, SO$_4^{2-}$, HCO$_3^-$, CO$_3^{2-}$, acetate, lactate, succinate, propionate, butyrate, ascorbate, citrate, maleate, folate, an amino acid derivative, or a nucleotide.

28. The polymer composition of claim 23 wherein said hydrophobic moiety is a substituted or unsubstituted, normal, branched or cyclic alkyl group having at least six carbon atoms.

29. The polymer composition of claim 28, wherein the hydrophobic moiety is an alkyl group of between about eight and twelve carbons.

30. The polymer composition of claim 28 wherein the hydrophobic moiety is an alkyl group of about ten carbons.

31. The polymer composition of claim 23 wherein the copolymer is crosslinked.

32. The polymer composition of claim 31 wherein the copolymer is crosslinked prior to substitution of the amine nitrogens.

33. The polymer composition of claim 31 wherein said polymer composition is crosslinked by means of a multifunctional crosslinking co-monomer, said co-monomer being present in an amount from about 0.5% to about 25% by weight, based upon total monomer weight.

34. The polymer composition of claim 33 wherein said crosslinking co-monomer is present in an amount from about 1% to about 10% by weight, based upon total monomer weight.

35. The polymer composition of claim 23, wherein the quaternary amine-containing moiety has the following formula:

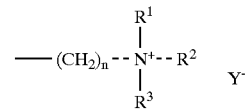

wherein,
R$^1$, R$^2$ and R$^3$ represent an alkyl group, wherein each R, independently, is a normal or branched, substituted or unsubstituted alkyl group having a carbon atom chain length of between about one to about twenty four carbon atoms,
n is an integer having a value of three or more, and
Y is a negatively-charged counterion.

36. The polymer composition of claim 35, wherein R$^1$, R$^2$ and R$^3$ are all methyl groups and n has a value between about three and about twelve carbons.

37. The polymer composition of claim 36, wherein n is 6.

38. The polymer composition of claim 36, wherein n is 8.

39. The polymer composition of claim 36, wherein n is 10.

40. The polymer composition of claim 35 wherein at least one of $R^1$, $R^2$ and $R^3$ is a hydrophobic alkyl group having from six to about twenty-four carbons the remainder of which each independently having from one to twenty-four carbons.

41. The polymer composition of claim 40 wherein the quaternary amine- containing moiety is 3-(dodecyldimethylammonio)propyl.

42. The polymer composition of claim 35 wherein at least two of $R^1$, $R^2$ and $R^3$ are hydrophobic alkyl groups having from six to about twenty-four carbons the remainder having from one to twenty-four carbons.

43. The polymer composition of claim 42 wherein the quaternary amine-containing moiety is 4-(dioctylmethylammonio)butyl.

44. The polymer composition of claim 35 wherein all three of $R^1$, $R^2$ and $R^3$ are hydrophobic alkyl groups having from six to about twenty-four carbons.

* * * * *